United States Patent [19]

Saotome

[11] Patent Number: 4,748,076

[45] Date of Patent: May 31, 1988

[54] WATER ABSORBENT FIBROUS PRODUCT AND A METHOD OF PRODUCING THE SAME

[75] Inventor: Kazuo Saotome, Tokyo, Japan

[73] Assignee: Hayashikane Shipbuilding & Engineering Co., Ltd., Japan

[21] Appl. No.: 829,668

[22] Filed: Feb. 13, 1986

[30] Foreign Application Priority Data

| Feb. 16, 1985 [JP] | Japan | 60-27570 |
| Jun. 22, 1985 [JP] | Japan | 60-136654 |
| Dec. 4, 1985 [JP] | Japan | 60-273896 |

[51] Int. Cl.$^4$ .................. A61F 13/18; A61L 15/00; A61L 15/01; D06M 15/263
[52] U.S. Cl. .................. 428/224; 8/115.62; 8/116.1; 8/DIG. 18; 128/132 D; 427/389.9; 427/392; 428/297; 428/361; 604/370; 604/371; 604/372; 604/376; 604/377
[58] Field of Search .......... 8/116.1, 115.62, DIG. 18; 427/389.9, 392; 428/297, 361, 290, 224; 604/365, 370, 371, 372, 375, 376, 377

[56] References Cited

U.S. PATENT DOCUMENTS

| 3,005,456 | 10/1961 | Graham, Jr. . | |
| 3,589,364 | 6/1971 | Dean et al. . | |
| 4,340,057 | 7/1982 | Bloch et al. | 604/372 |
| 4,354,487 | 10/1982 | Oczkowski et al. | 604/370 |
| 4,423,184 | 12/1983 | Kopolow et al. | 604/372 |
| 4,443,492 | 4/1984 | Roller | 604/372 |

FOREIGN PATENT DOCUMENTS

| 51-144476 | 12/1976 | Japan . |
| 58-84804 | 5/1983 | Japan . |

Primary Examiner—James C. Cannon
Attorney, Agent, or Firm—Sprung Horn Kramer & Woods

[57] ABSTRACT

A water absorbent fibrous product comprising a fibrous cellulosic material impregnated with a water absorbent acrylic polymer and a fibrous material, which is produced by a method in which an aqueous solution of a monomeric component comprising acrylic acid and a radical initiator is diffused in a fibrous cellulosic material and heated, followed by blending with a fibrous material. The fibrous product exhibits a high water absorbency, and finds applications as high-quality disposable diapers, sanitary napkins, surgical pads, surgical sheets, paper towels or the like.

18 Claims, No Drawings

WATER ABSORBENT FIBROUS PRODUCT AND A METHOD OF PRODUCING THE SAME

This invention relates to a water absorbent fibrous product and a method of producing the same. More particularly, this invention is concerned with a water absorbent fibrous product comprising a fibrous cellulosic material impregnated with a water absorbent acrylic polymer and a fibrous material, and a method for producing the same in which an aqueous solution of a monomeric component is diffused in a fibrous cellulosic material and heated, followed by blending with a fibrous material. The water absorbent fibrous product can be used as a disposable diaper, a sanitary napkin, a surgical pad, a surgical sheet, a paper towel or the like.

Known in the art are water absorbent fibrous products comprising a fibrous substrate such as tissue paper and absorbent pulp and spread over the substrate, powders of a water absorbent acrylic polymer. They are used for production of a disposable diaper, a sanitary napkin or the like. They have a sufficient water absorbency due to the presence of the powders of water absorbent polymer spread thereover, which acrylic polymer is usually insolubilized to water by crosslinking. However, they have a drawback that due to the difference in properties such as specific gravity and configuration between the acrylic polymer and the fibrous substrate, the powders of water absorbent acrylic polymer are removed from the fibrous substrate and distributed unevenly by the vibration exerted thereupon or the like during the transportation of the product, etc. Moreover, the trouble occurs that a gel formed as a result of water absorption of the water absorbent polymer is separated from the fibrous substrate and comes to direct contact with the skin of a person wearing the product to give an uncomfortable feeling to the person. Moreover, the production of the water absorbent acrylic polymer is accompanied by the following problem. When a radical initiator is added to an aqueous solution containing 40% by weight or more of acrylic acid neutralized with sodium hydroxide to give a neutral pH value and the resulting mixture is heated, there rapidly occurs a polymerization reaction while producing a partially self-crosslinked acrylic polymer. After the initiation of the polymerization reaction, the viscosity of the aqueous solution increases and a gel is formed with the progress of crosslinking. While the polymerization reaction is accelerated due to the elevation of the temperature which is attributed to the heat of reaction, evaporation of the steam out of the reaction system is hindered due to the increased viscosity and the gelation of the mixture. As a result, removal of the heat of reaction becomes difficult, and the reaction proceeds uncontrollably with the formation of a popcorn-like material. Especially when the reaction system becomes a gel, generally known "gel effect" occurs to further increase the reaction rate, thereby causing controlling of the polymerization reaction to be more difficult. To obviate such a difficulty, there have been proposed various polymerization methods, including a reverse phase suspension polymerization method in which polymerization is effected in a dispersion having fine particles of the aqueous reaction solution dispersed in an oily phase. In this method, it is possible to polymerize acrylic acid in a high concentration aqueous solution. However, this method is disadvantageous because in this method a large amount of a hydrocarbon solvent must be used and a countermeasure against a fire is required, thereby inevitably leading to an increase in manufacturing cost. Further, in this method, it is difficult to practice a continuous process.

Therefore, there is still a strong demand in the art for a water absorbent fibrous product comprising a fibrous structure and a water absorbent polymer component integrated therewith, which product behaves just as the fibrous structure per se has an absorbency.

U.S. Pat. No. 3,005,456 discloses a method for improving the absorbency of a fibrous cellulosic material in which the surface portion thereof is subjected to carboxymethylation. In U.S. Pat. No. 3,589,364, there is disclosed a method in which a carboxymethylated fibrous cellulose is subjected to crosslinking for insolubilization. Japanese Patent Application Laid-Open Specification No. 51-144476/1976 discloses a water absorbent fibrous material produced by a method in which a fibrous carboxymethyl cellulose is graft-polymerized with acrylonitrile and the graft-polymerization product is hydrolyzed.

The method as disclosed in U.S. Pat. No. 3,005,456 in which carboxymethylation of a fibrous cellulose is effected in a level at which solubilization of the cellulose does not occur does not produce a fibrous product having a high degree of water absorbency. Further, the method is disadvantageous from the economical point of view, because the carboxymethylation is effected by reacting the cellulose with chloroacetic acid in a propanol solution. On the other hand, the method as disclosed in Japanese Patent Application Laid-Open Specification No. 51-144476/1976 in which absorbent polymer segments are grafted to a fibrous carboxymethyl cellulose may produce a water absorbent fibrous product improved in water absorbency, but inevitably leads to an increase in cost when the method is practiced on a commercial scale because expensive apparatuses and time-consuming operations are required.

Moreover, it has been proposed to utilize a method in which a solution of a water soluble polymer such as maleic acid copolymer is applied onto a fibrous material such as non-woven fabric and the resulting water soluble polymer-applied fibrous material is subjected to heat treatment in the presence of a crosslinking agent during the drying step to insolubilize the water soluble polymer, thereby imparting a water absorbency thereto (see Japanese Patent Application Laid-Open Specification No. 58-84804/1983). In this method, the aqueous solution of the polymer has a high viscosity and therefore is difficult to be uniformly permeated into the fibrous material unless the aqueous solution is highly diluted to a solution having an extremely low concentration. Moreover, the method is disadvantageous in that it is difficult to control the crosslinking reaction and to effect uniform crosslinking and crosslinking density, thereby leading to insufficient absorbency.

In most cases, fibrous products containing a water absorbent polymer are used for the production of disposable articles. Hence, low cost is the prime requirement for such absorbent fibrous products. However, the efforts for providing low-cost water absorbent fibrous products have not been fully successful.

As is apparent from the foregoing, all of the prior art methods and products are advantageous in some points but disadvantageous in other points.

With a view to providing a novel fibrous product improved in absorbency which is free from the above-mentioned drawbacks, we have made extensive and intensive studies.

As a result, it has unexpectedly been found that a fibrous cellulosic material impregnated with an acrylic polymer can be stably and efficiently produced by diffusing an aqueous mixture of acrylic acid and a radical initiator in a fibrous cellulosic material, followed by heating, and that a product obtained by blending such a fibrous cellulosic material impregnated with a crosslinked acrylic polymer with a fibrous material can advantageously be utilized as a disposable diaper, a sanitary napkin, a surgical pad, a surgical sheet, a paper towel or the like. Based on these novel findings, the present invention has been completed.

It is, therefore, an object of the present invention to provide a novel water absorbent fibrous product which exhibits an excellent water absorbency and which can be used as a high-quality disposable diaper, a high-quality sanitary napkin, a high-quality surgical pad, a high-quality surgical sheet, a high-quality paper towel or the like.

It is another object of the present invention to provide a novel method of producing such an excellent water absorbent fibrous product which method ensures stable, efficient operations and which is free from the above-mentioned drawbacks of the prior art.

The foregoing and other objects, features and advantages of the present invention will be apparent to those skilled in the art from the following detailed description and applended claims.

In one aspect of the present invention, there is provided a water absorbent fibrous product comprising a fibrous cellulosic material impregnated with a water absorbent acrylic polymer and a fibrous material which product is produced by a method described below.

In another aspect of the present invention, there is provided a method of producing a water absorbent fibrous product which comprises the steps of:

(1) providing an aqueous solution comprised of water, a monomeric component comprising acrylic acid and a radical initiator;

(2) diffusing the aqueous solution in a fibrous cellulosic material to obtain an aqueous mixture;

(3) heating the aqueous mixture to effect radical polymerization of said monomeric component to form a crosslinked acrylic polymer, thereby obtaining a polymerization product containing the fibrous cellulosic material impregnated with said polymer; and (4) blending the polymerization product with a fibrous material.

With respect to Step 1 of the method of the present invention, the monomeric component may further comprise at least one member selected from the group consisting of a water soluble copolymerizable monomer and a water soluble crosslinkable polyfunctional monomer. As the suitable water soluble copolymerizable monomer, there may be mentioned, for example, methacrylic acid, maleic acid, fumaric acid, itaconic acid, acrylamide, methacrylamide and mixtures thereof. The acrylic acid content of the monomeric component is generally at least 70% by weight.

In the present invention, the monomeric component concentration of the aqueous solution is not critical. However, the aqueous solution may preferably contain 20 to 50% by weight, based on the aqueous solution, of a monomeric component of which 60 to 90% of the carboxyl groups are in the form of an alkali metal salt. Conversion of 60 to 90%, preferably 60 to 80%, of the carboxyl groups of the monomeric component into an alkali metal salt may be effected according to various methods. For example, it may be effected by adding a predetermined amount of a caustic alkali solution, such as sodium hydroxide solution, to the solution of the monomeric component. The above-mentioned aqueous solution generally exhibits a neutral pH in the range of 5 to 8.

In the present invention, the aqueous solution may also comprise a water soluble polymer selected from starch and a cellulose derivative such as carboxymethyl cellulose. The soluble polymer concentration of the aqueous solution may be 20% by weight or less.

In the present invention, the polymer molecules may be crosslinked by (1) self-crosslinking, (2) copolymerization with a crosslinkable polyfunctional monomer and (3) post-crosslinking of the produced polymers by a crosslinking agent.

Self-crosslinking may occur when the aqueous solution contains 40% by weight or more of a monomeric component.

As the crosslinkable polyfunctional monomer to be used in the copolymerization, there may be mentioned, for example, N,N'-methylenebisacrylamide, ethylene glycol bisacrylate, polyethylene glycol bisacrylate, and the like.

As the post-crosslinking agent to be used for the post-crosslinking, there may be mentioned, for example, diethylene glycol, glycerin, ethylene glycol diglycidyl ether and the like.

Of the crosslinking methods, copolymerization with a crosslinkable polyfunctional monomer and post-crosslinking of the produced polymers by a crosslinking agent are generally preferred from the viewpoint of crosslinking density.

In the present invention, a water soluble radical initiator may be added to the aqueous solution in an amount of 0.001 to 1.0%, based on the total weight of the aqueous solution. As the suitable initiator, there may be mentioned, for example, a persulfate compound such as ammonium persulfate, sodium persulfate and potassium persulfate, and a peroxy compound such as hydrogen peroxide and peracetic acid. To lower the decomposition temperature of the initiator and thus the polymerization temperature, a reducing agent such as sulfite compound may be added to the aqueous solution in accordance with the known redox initiator system. The acrylic polymer formed by polymerization of the monomeric component is water absorbent and swells to a high degree but it is not soluble in water.

In step 2 of the method of the present invention, the aqueous solution is uniformly diffused in a fibrous cellulosic material. When the amount of the polymer produced by polymerization of the monomeric component exceeds that of the fibrous cellulosic material, block-form substances may result which cannot be readily brought to pieces, thereby causing it difficult to effect uniform mixing with a fibrous material in the next step. Therefore, in the present invention, the amount of the polymer produced from the monomeric component is generally not greater than that of the fibrous cellulosic material. It is preferred that the amount ratio of monomeric component to cellulosic material be in the range of from 5/95 to 50/50, especially from 10/90 to 30/70.

The kind of the fibrous cellulosic material to be employed in the present invention is not critical. However, it is generally preferred that a chemically purified wood pulp, a chemically purified cotton linter pulp, a chemically purified cotton, a rayon fiber or the like be employed. The term "pulp" used herein means a mass of fibrous pieces composed of cellulose as the major component. The size of the fibrous cellulosic material is not critical. However, in the present invention, it is preferred that the fibrous cellulosic material have a length of 0.5 to 10 mm and a diameter of 1 to 50 denier. The aqueous solution can be readily diffused in the fibrous cellulosic material. For example, in the cellulosic material can be readily diffused the aqueous solution in an amount of about 10 times that of the cellulosic material.

It is to be noted that in addition to the belowdescribed controlling of the polymerization reaction, the incorporation of a fibrous cellulosic material has an effect of accelerating the drying of water-containing product and also an effect of improving of the absorption rate of the ultimate product. These effects will be easily understood from the fact that the incorporation of a fibrous cellulosic material renders the ultimate solid product porous.

In step 3 of the method of the present invention, the aqueous mixture obtained in the preceding step is heated to effect radical polymerization; of the monomeric component to form a crosslinked acrylic polymer. The polymerization reaction is generally effected in an inert atmosphere. When a radical initiator is employed, the polymerization reaction may be initiated at a temperature of about 60° C. or more. However, the polymerization initiation temperature may be lowered by employing a redox initiator system, as mentioned hereinbefore. Since the polymerization reaction is accompanied by generation of heat, the temperature of the mixture elevates unless external cooling is effected. When the temperature of the mixture exceeds 100° C., however, rapid evaporation of water from the mixture occurs, thereby enabling the temperature of the mixture to be controlled at a temperature not exceeding 110° C. Therefore, although external cooling may be effected to maintain the temperature of the reaction mixture at, for example, 100° C. or less, the intended polymerization product can be obtained without the aid of external cooling. With respect to external cooling, it may be readily effected, for example, by circulating cooled nitrogen gas through the mixture. Circulation of nitrogen gas is facile due to the larger content of fibrous cellulosic material as mentioned hereinbefore. The temperature of the mixture can be readily controlled at less than 100° C., for example, 80° C. by circulation of cooled nitrogen gas through the mixture.

In the polymerization step, it is important to employ an appropriate heating system for initiating the polymerization reaction. It is preferred that an aqueous mixture, in which a redox initiator system as mentioned hereinbefore may or may not be contained, be heated by the known high-frequency induction heating technique or by a technique in which heating and cooling of the mixture is effected by the boiling vapor of a hydrocarbon solvent such as n-hexane or n-heptane having a boiling point of from 60° to 100° C. which is suitable to allow the polymerization reaction to proceed. Since the presence of oxygen retards the polymerization reaction, it is preferred that the reaction vessel be evacuated or the air in the vessel be replaced by nitrogen gas. During such procedures and the polymerization reaction, rapid evaporation of water may occur. Hence, the concentration of the aqueous solution is to be determined taking into account such evaporation of water from the mixture. The polymerization reaction may be usually completed within about 60 minutes.

The polymerization product containing the fibrous cellulosic material impregnated with the crosslinked acrylic polymer may preferably be brought to pieces. Bringing the polymerization product to pieces may be carried out in the dry state or in the wet state. Bringing the polymerization product to pieces in the dry state may be carried out using customary breaking machines well known in the textile industries. Bringing the polymerization product to pieces in the wet state may be carried out in an aqueous solvent. As the aqueous solvent, a mixture of methanol and water may be preferably employed because it prevents the polymer from swelling to an excessive extent.

In step 4 of the method of the present invention, the polymerization product, preferably after being brought to pieces, is blended with a fibrous material to obtain the ultimate fibrous product. The method of blending the polymerization product with a fibrous material is not critical. It may be readily carried out using blending machines well known in the textile industries or in the wet state in an aqueous solvent, for example, a mixture of methanol and water.

The length and diameter of the fibrous material is in substantially the same range as described hereinbefore with respect to the fibrous cellulosic material to be employed in the present invention.

The kind of fibrous material to be employed in the present invention is not critical. It may be a natural fiber or a synthetic fiber. As the suitable natural fiber, there may be mentioned, for example, a fibrous cellulosic material to be employed in step 2 described above and a wool fiber. As the suitable synthetic fiber, there may be mentioned, for example, a polyolefin fiber, a polyester fiber, a nylon fiber and a polyacrylonitrile fiber.

The ratio of the amount of the polymerization product to the amount of the fibrous material to be blended therewith is not critical, and may be widely varied according to the use of the ultimate fibrous product. However, it is generally preferred that the polymerization product be blended with the fibrous material in such an amount ratio that the acrylic polymer content of the blended product consisting of the polymerization product and the fibrous material is at least 2% by weight.

The polymerization product obtained in step 3 and the ultimate fibrous product obtained in step 4 may find applications in the same field. However, the latter is excellent as compared with the former as indicated below. That is, a comparison of the ultimate fibrous product (A) obtained in step 4 to the polymerization product (B) obtained in steps leads to the following findings:

(1) in the dry state, A gives a soft touch as that given by the corresponding fiber material not impregnated with any polymer, whereas B gives a rigid touch;

(2) in the water absorbed, swollen state, A gives a touch of remarkably decreased stickiness close to that of the corresponding fiber material not impregnated with any polymer, whereas B gives a sticky touch due to the polymer gel; and (3) with respect to the water absorbency per g of the polymer, A is close to the polymer per se whereas B exhibits a much lower value than that of the polymer per se.

As regards (3) above, the absorbency improvement of A can be attributed to the fact that in the case of A, the polymerization product is uniformly dispersed in a fibrous material not containing any polymer so that the restriction preventing the polymer from absorbing water and swelling is remarkably removed, whereas in the case of B, the impregnated polymer is put under constraint due to entangled fibers at water absorption and swelling so that the polymer cannot fully exhibit its absorbing capacity.

The ultimate fibrous product per se can be used as a disposable diaper, a sanitary napkin, a surgical pad, a surgical sheet, a paper towel or the like. The ultimate fibrous product, according to need, may be processed into a sheet or mat or a non-woven fabric before such applications. Such processing may be carried out by utilizing known techniques.

For example, a non-woven fabric having a polymer content of about 5% prepared in the dry state using a pulp as the fibrous material finds a wide variety of applications in the production of a paper towel or the like, since such a non-woven fabric has an absorbency of 2 to 3 times that of the corresponding fabrics containing no polymer. In this case, incorporation of a rayon fiber serves to improve the mechanical strength of the fibrous product. Non-woven fabrics based on a synthetic fiber such as polypropylene polyester, nylon, polyacrylonitrile and the like may also be mixed with the fibrous cellulosic material impregnated with the crosslinked acrylic polymer, thereby imparting an excellent absorbency to the non-woven fabrics which are hydrophobic in nature.

The fibrous product according to the present invention has a structure in which a fibrous cellulosic material impregnated with a polymer is uniformly dispersed in a fibrous material. Therefore, the fibrous product is free from the problem of separation due to gel formation with the progress of water absorption, and hence does not give any uncomfortable feeling, as different from a fibrous product having powdery form of polymer spread thereover.

The present invention will be illustrated in more detail with reference to the following Examples, which should not be construed to be limiting the scope of the present invention.

EXAMPLE 1

In 250 parts by weight of water were dissolved 72 parts by weight of acrylic acid, 33 parts by weight of sodium hydroxide (purity: 93%) and 0.05 part by weight of N,N'-methylenebisacrylamide. To the resulting solution was added 0.3 part by weight of potassium persulfate to prepare an aqueous solution having an acrylic content of 25% and a pH value of 5.6.

85 parts by weight of the thus prepared aqueous solution was sprayed over 60 parts by weight of absorbent cotton and allowed to uniformly diffuse into the absorbent cotton. The aqueous solution-diffused absorbent cotton was put in a closed vessel. The content of the vessel was flushed with nitrogen gas and heated at a temperature of 95° C. for 15 minutes to effect polymerization of the acrylic component. During the course of polymerization, a vigorous evolution of steam was observed. After completion of the polymerization, the resulting polymerization product was dried. By weight measurement, it was found that the polymerization product contained 26% by weight of a polymer based on the weight of the polymerization product. Then 50 parts by weight of the polymerization product was brought to pieces and the pieces were uniformly mixed with 100 parts by weight of absorbent cotton to obtain a fibrous product. The fibrous product contained 8.6% by weight of the polymer.

1 g of the fibrous product was placed in 200 g of water. 30 minutes later the fibrous product was taken out on a wire netting. The fibrous product weighed 43 g. On the other hand, 1 g of untreated absorbent cotton weighed 12 g after the water absorption thereof. This shows that 1 g of the polymer absorbed 380 g of water. When 1 g of the fibrous product was placed in 0.9% by weight aqueous sodium chloride solution, the weight of the product increased to 17 g which corresponds to 60 g water absorption per g of the polymer.

For comparison 31 parts by weight of the above-obtained aqueous solution was sprayed over 50 parts by weight of absorbent cotton, allowed to uniformly diffuse into the absorbent cotton, and heated in a manner as described above to obtain a polymerization product having a polymer content of 8.6%. The obtained product gave a hard feeling as compared with the above fibrous product, and had a water absorbency of 38 (g/g), that is, 1 g of the polymer absorbed 310 g of water.

EXAMPLES 2 to 5

Each of methacrylic acid, maleic acid and soluble starch was separately added as a minor component to acrylic acid. To the resulting solution were further added N,N'-methylenebisacrylamide (hereinafter referred to simply as "MBAM") as a crosslinking agent and potassium persulfate (hereinafter referred to simply as "KPS") as an initiator to prepare an aqueous solution having an monomeric content of 30% by weight of which the pH was adjusted to a neutral value with sodium hydroxide. Compositions of the prepared solutions are shown in Table 1.

TABLE 1

| Example | Composition of aqueous solution to be polymerized (parts by weight) | | | |
|---|---|---|---|---|
|  | 2 | 3 | 4 | 5 |
| Acrylic acid | 72 | 64.8 | 64.8 | 72 |
| Methacrylic acid | — | 8.6 | — | — |
| Maleic acid | — | — | 5.8 | — |
| Soluble starch | — | — | — | 8 |
| MBAM | 0.05 | 0.05 | 0.05 | 0.05 |
| KPS | 0.15 | 0.15 | 0.15 | 0.15 |
| Water | 192 | 212 | 190 | 211 |
| NaOH (purity 93%) | 34 | 34 | 34 | 34 |
| pH | 6.6 | 6.6 | 6.6 | 6.6 |

50 parts by weight of each of the prepared solutions was sprayed over 60 parts by weight a chemically purified cotton linter pulp, allowed to uniformly diffuse into the pulp and heated under nitrogen atmosphere at 100° C. for 15 minutes to effect polymerization. Each of the aqueous solutions had a monomeric content of 30% by weight, and the polymerization products had a polymer content of 20% by weight.

Thereafter, each of the polymerization products was dried, brought to pieces and the pieces were mixed with the same amount of cotton linter pulp to prepare a fibrous product containing 10% by weight of a polymer. Absorbencies of the fibrous products were measured in accordance with the procedure as described in Example 1. Results are shown in Table 2.

TABLE 2
Absorbency of fibrous product

| Examples | Water (g/g) | 0.9% NaCl solution (g/g) |
| --- | --- | --- |
| 2 | 52 | 16.5 |
| polymer (calculated) | 420 | 65 |
| 3 | 49 | 15.5 |
| polymer (calculated) | 390 | 55 |
| 4 | 50 | 16.0 |
| polymer (calculated) | 400 | 60 |
| 5 | 47 | 15.2 |
| polymer (calculated) | 370 | 52 |

EXAMPLE 6

34 parts by weight of sodium hydroxide (purity: 93%) was dissolved in 150 parts by weight of water. To the resulting solution was added 72 parts by weight of acrylic acid. After cooling, 0.5 part by weight of potassium persulfate was added to prepare an aqueous solution having an acrylic content of 35% by weight and a pH value of 5.7.

57 parts by weight of the above-prepared aqueous solution was sprayed over 60 parts by weight of a purified cotton linter pulp, and allowed to uniformly diffuse into the pulp. Then, the resulting mixture was heated under heated nitrogen atmosphere at a temperature of 95° C. for 15 minutes thereby allowing polymerization to proceed with evolution of steam. During the process of polymerization, 22 parts by weight of water was evaporated, thereby leaving 95 parts by weight of a polymerization product. The polymerization product was dried to have a polymer content of 25% by weight. The thus obtained polymerization product was brought to pieces and the pieces were uniformly mixed with a two-fold amount of cotton linter pulp to obtain a fibrous product. The fibrous product had absorbancies as shown in Table 3.

TABLE 3

| | Absorbencies (g/g) | |
| --- | --- | --- |
| | water | 0.9% NaCl Solution |
| fibrous product | 59 | 16 |
| polymer (calculated) | 590 | 62 |

EXAMPLES 7 and 8

In 190 parts by weight of water were dissolved 72 parts by weight of acrylic acid, 34 parts by weight of sodium hydroxide (purity: 93%), 0.05 part by weight of N,N'-methylenebisacrylamide and 0.1 part by weight of potassium persulfate to prepare an aqueous solution having an acrylic content of 30% by weight and a pH value of 5.7.

85 parts by weight of the above-prepared aqueous solution was sprayed over 60 parts by weight of a chemically purified wood pulp, and allowed to uniformly diffuse into the pulp. Thereafter, the mixture was heated at 100° C. for 10 minutes under nitrogen atmosphere to obtain a polymerization product. The polymerization product was dried to have a polymer content of 29% by weight.

To 300 parts by weight of a 50/50 by volume mixture of water and methanol were added 20 parts by weight of the above-obtained polymerization product and 50 parts by weight of wood pulp. The resulting mixture was vigorously stirred to bring the polymerization product to pieces. Thereafter, the mixture was taken out on a wire-netting to make a sheet. The sheet was dried to obtain a non-woven fabric having a polymer content of 8.2%. The obtained non-woven fabric exhibited an absorbency of 38 g/g in water. On the other hand, the corresponding non-woven fabric which did not contain any polymer exhibited an absorbency of 8 g/g in water. Hence, the absorbency of the polymer is calculated to be 370 g/g.

Separately, 20 parts by weight of the aboveobtained polymerization product and 60 parts by weight of a polyethylene staple having a length of about 1 cm were brought to pieces and mixed with each other in a 50/50 by volume mixture of water and methanol containing a small amount of a polyvinylacetate type binder. The resulting mixture was taken out on a wire-netting to prepare a non-woven fabric in substantially the same manner as described above. The obtained non-woven fabric had a polymer content of 7.2% by weight and a water absorbency of 23 g/g.

The above description of the invention are set forth only by way of illustration. As will be apparent to those skilled in the art, other variations and modifications can readily be employed without departing from the spirit and scope of the invention above and claimed below.

What is claimed is:

1. A water absorbent fibrous product produced by a method comprising the steps of:
   (1) providing an aqueous solution comprised of water, a monomeric component comprising a water-soluble cross-linkable polyfunctional monomer, acrylic acid, 60 to 90% of the carboxyl groups of said acrylic acid being in the form of an alkali metal salt, and a radical initiator;
   (2) diffusing the aqueous solution in a fibrous cellulosic material in such proportions that the amount ratio of said monomeric component to said cellulosic material is in the range of from 5/95 to 50/50 to obtain an aqueous mixture;
   (3) heating the aqueous mixture at a temperature of 60° C. or more to effect radical polymerization of said monomeric component to form a crosslinked acrylic polymer, thereby obtaining a polymerization product containing the fibrous cellulosic material impregnated with said polymer, followed by bringing to pieces; and
   (4) blending the polymerization product with a fibrous material.

2. A product according to claim 1, wherein in step (3), said polymerization product is dried before bringing to pieces.

3. A product according to claim 1, wherein said aqueous solution contains said monomeric component in an amount of from 20 to 50% by weight, based on said aqueous solution.

4. A product according to claim 1, wherein said amount ratio of monomeric component to cellulosic material is in the range of from 10/90 to 30/70.

5. A product according to claim 1, wherein 60 to 80% of the carboxyl groups of said acrylic acid are in the form of an alkali metal salt.

6. A product according to claim 1, wherein said radical initiator is employed in an amount of from 0.001 to 1.0% by weight, based on said aqueous solution.

7. A product according to claim 1, wherein said monomeric component further comprises a water soluble copolymerizable monomer.

8. A product according to claim 1, wherein said aqueous solution further comprises at least one member selected from the group consisting of a water soluble post-crosslinking agent, a water soluble starch and a water solubloe cellulose derivative.

9. A product according to claim 7, wherein said aqueous solution comprises water, 20 to 50% by weight, based on said aqueous solution, of a monomeric component comprising acrylic acid, a water soluble copolymerizable monomer and a water soluble crosslinkable polyfunctional monomer together with a radical initiator,
the amount ratio of said acrylic acid to said copolymerizable monomer being at least 70/30 by weight,
said copolymerizable monomer being selected from the group consisting of methacrylic acid, maleic acid, fumaric acid, itaconic acid, acrylamide, methacrylamide and mixtures thereof,
60 to 90% of the carboxyl groups of each of said acrylic acid, methacrylic acid, maleic acid, fumaric acid and itaconic acid being in the form of an alkali metal salt.

10. A product according to claim 1, wherein said cellulosic material is a member selected from the group consisting of a chemically purified wood pulp, a chemically purified cotton linter pulp, a chemically purified cotton and a rayon fiber.

11. A product according to claim 1, wherein said fibrous material is a fibrous cellulosic material, a wool fiber or a synthetic fiber.

12. A product according to claim 11, wherein said synthetic fiber is a member selected from the group consisting of a polyolefin fiber, a polyester fiber, a nylon fiber and a polyacrylonitrile fiber.

13. A product according to claim 1, wherein said polymerization product is blended with said fibrous material in such an amount ratio that the acrylic polymer content of the blended product consisting of said polymerization product and said fibrous material is at least 2% by weight.

14. A product according to claim 1, which is in the form of a sheet or a non-woven fabric.

15. A product according to claim 1, wherein said radical initiator is a water soluble persulfate compound.

16. A method of producing a water absorbent fibrous product which comprises the steps of:
(1) providing an aqueous solution comprised of water, a monomeric component comprising a water soluble cross-linkable polyfunctional monomer, acrylic acid, 60 to 90% of the carboxyl groups of said acrylic acid being in the form of an alkali metal salt, and a radical initiator;
(2) diffusing the aqueous solution in a fibrous cellulosic material in such proportions that the amount ratio of said monomeric component to said cellulosic material is in the range of from 5/95 to 50/50 to obtain an aqueous mixture;
(3) heating the aqueous mixture at a temperature of 60° C. or more to effect radical polymerization of said monomeric component to form a crosslinked acrylic polymer, thereby obtaining a polymerization product containing the fibrous cellulosic material impregnated with said polymer, followed by bringing to pieces; and
(4) blending the polymerization product with a fibrous material.

17. A method according to claim 16, wherein 60 to 80% of the carboxyl groups of said acrylic acid are in the form of an alkali metal salt.

18. A method according to claim 16, wherein said radical initiator is a water soluble persulfate compound.

* * * * *